(12) United States Patent
Milbank (10) Patent No.: US 7,785,325 B1
(45) Date of Patent: Aug. 31, 2010

(54) MULTI-ARTICULATED FRACTURE FIXATION DEVICE WITH ADJUSTABLE MODULUS OF RIGIDITY

(76) Inventor: Miles C. Milbank, 458 Appaloosa Ct., Santa Rosa, CA (US) 95401

( * ) Notice: Subject to any disclaimer, the term of this patent is extended or adjusted under 35 U.S.C. 154(b) by 579 days.

(21) Appl. No.: 11/671,420

(22) Filed: Feb. 5, 2007

Related U.S. Application Data (60) Provisional application No. 60/765,413, filed on Feb. 3, 2006.

(51) Int. Cl.
*A61B 17/72* (2006.01)
(52) U.S. Cl. .................... 606/62; 606/259; 403/123
(58) Field of Classification Search ............ 606/62–68, 606/254–260, 300–331, 80, 103; 403/123; 411/383, 392; 63/38
See application file for complete search history.

(56) References Cited

U.S. PATENT DOCUMENTS

| | | | | |
|---|---|---|---|---|
| 3,283,640 A * | 11/1966 | Teizo | ............................ | 411/33 |
| 3,846,846 A * | 11/1974 | Fischer | .................... | 623/23.18 |
| 3,858,578 A * | 1/1975 | Milo | .......................... | 600/229 |
| 4,190,044 A | 2/1980 | Wood | | |
| 5,645,545 A | 7/1997 | Bryant | | |
| 5,649,925 A * | 7/1997 | Alacreu | ..................... | 606/86 A |
| 5,879,352 A * | 3/1999 | Filoso et al. | ................... | 606/62 |
| 5,997,582 A | 12/1999 | Weiss | | |
| 6,120,504 A | 9/2000 | Brumback | | |
| 6,296,644 B1 * | 10/2001 | Saurat et al. | ................. | 606/256 |
| 6,443,992 B2 * | 9/2002 | Lubinus | ................... | 623/23.18 |
| 6,755,862 B2 * | 6/2004 | Keynan | ................... | 623/16.11 |
| 2003/0109932 A1* | 6/2003 | Keynan | ................... | 623/23.18 |
| 2005/0038432 A1* | 2/2005 | Shaolian et al. | ............... | 606/61 |
| 2008/0294163 A1* | 11/2008 | Chou et al. | .................... | 606/62 |

* cited by examiner

*Primary Examiner*—Eduardo C Robert
*Assistant Examiner*—Steven J Cotroneo
(74) *Attorney, Agent, or Firm*—Craig M. Stainbrook; Stainbrook & Stainbrook, LLP

(57) ABSTRACT

A multi-articular intramedullary fracture fixation device having a adjustable modulus of rigidity. The implant apparatus includes modular tensioning elements that can be disposed in a ball-and-socket linear array along a length of connecting wire within a medullary canal. The connecting wire includes a threaded end and a stop member at the opposite end, and when a lock nut is threadably disposed on the threaded end and tightened, at least two of the tensioning elements in the array may be swiveled relative to one another and arranged to introduce curvature as desired along the length of the array. Tightening the lock nut is also employed to adjust the modulus of rigidity to be retained during healing.

1 Claim, 5 Drawing Sheets

MULTI-ARTICULATED FRACTURE FIXATION DEVICE WITH ADJUSTABLE MODULUS OF RIGIDITY

CROSS REFERENCES TO RELATED APPLICATIONS

The present application claims the benefit of the filing date of U.S. Provisional Patent Application Ser. No. 60/765,413, filed Feb. 3, 2006.

STATEMENT REGARDING FEDERALLY SPONSORED RESEARCH OR DEVELOPMENT

Not applicable.

THE NAMES OR PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

The present invention relates generally to medical devices for reduction, stabilization, and fixation of bone fractures, and more particularly to an articulated fracture fixation device with an adjustable modulus of rigidity, or elasticity in shear.

2. Discussion of Related Art Including Information Disclosed Under 37 CFR 1.97, 1.98

Intramedullary nailing of fractures was developed by Gerhard Kuntscher in Germany in the early 1940's. In the ensuing decades, this technique has come to be accepted as standard treatment for a middle-third shaft fracture of a long bone in the human body. While any long bone can be indicated for treatment with an intramedullary device, the most common application for this technique is in the femur and in the tibia.

While many different devices have been developed and utilized over the years, the technique has changed little. The procedure requires that the medullary canal of the bone be opened at either end of the bone. A guide rod is then placed lengthwise through the canal and across the fracture site while the fracture is reduced (the bone fragments returned to anatomical position). The medullary canal is then prepared for the implant, most commonly by systematically reaming in steps over and along a portion of the length of the guide rod. Once the canal is prepared, a properly sized implant is selected and installed over the guide rod, thereby effecting stabilization of the fracture. The guide rod is then removed and the surgical approach site is closed. The patient can begin rehabilitation shortly thereafter, and much sooner than had the fracture been fixed by earlier means, such as traction or a plaster cast.

In its essential form, an intramedullary nail is nothing more than a stabilization device that functions as a kind of internal splint. More elaborate devices have allowed for rotational stabilization and for proximal and distal fixation with varying degrees of success and utility.

However, all of the devices to date are poorly matched to the human anatomy. While an average curvature of the long bones can be applied to the manufacture of an array of implants to approximate the anatomy of most of the population, it is impossible to ensure that any implant will be absolutely correct in any given application.

Accordingly, an improved intramedullary device to reduce, stabilize, and fix fractures is needed, one, specifically, that may be tailored in size and shape to the particular patient and the particular conditions of the fracture and bone configuration encountered by the surgical team.

Improvements to the customary approach to fracture fixation have been proposed and are disclosed and discussed in the following exemplary patents.

U.S. Pat. No. 6,755,862, to Keynan, discloses an intramedullary support strut for a long bone for anchoring and fixation. The strut comprises nested telescopic members having retraced and extended configurations. In the retracted configuration, the strut is compact and may be inserted into position aligned with a shaft made in the medullary canal via a portal made in the lateral cortex of the bone. The strut may then be telescopically extended into the medullary canal to provide the required support.

U.S. Pat. No. 5,997,582, to Weiss, discusses the use of an expandable balloon to stabilize and fix a femoral head after hip replacement surgery.

U.S. Pat. No. 5,645,545, to Bryant, shows a self-reaming intramedullary nail that includes a rotatable reaming head mounted to the distal end of the cannulated nail body. A detachable drive shaft connects reaming head through nail body to a conventional rotational drill device. Reaming head and drive shaft have longitudinal bores that when connected form a passage for receiving a guide wire.

U.S. Pat. No. 4,190,044, to Wood, teaches a telescoping Intramedullary pin having a main body or base which is inserted in a drilled out marrow cavity of one-half of the broken bone. A portion of the marrow of the cooperating half of the broken bone is drilled out to accept the telescoping plunger which is positioned in the base. The two halves of the bone are brought together and the telescopic plunger is forced from the base into the drilled out marrow cavity by a stainless steel wire which is connected to the bottom of the telescoping pin and extends out of the bone cavity through the fracture. When the plunger is extended to its desired length, the stainless steel wire is cut and removed from the bone. The telescoping plunger is prevented from returning to the interior of the base by a series of ridges spaced longitudinally along the body of the plunger, which cooperate with faces of the resilient side walls of the base to prevent the reinsertion of the plunger into the base by providing an obstacle against which the ridges abut when return force is applied to the plunger.

U.S. Pat. No. 6,120,504, to Brumback, et al, discloses an intramedullary nail having a longitudinal centerline extending between a distal end and a proximal end. The nail defines a proximal attachment orientation adjacent the proximal end. The nail also defines a left distal bore and a right distal bore adjacent the distal end. The left distal bore and the right distal bore are anteverted in different directions about the longitudinal centerline with respect to the proximal attachment orientation. Thus the same nail can be used in an interlocking, reconstructive or retrograde fashion.

The foregoing patents and other prior art reflect the current state of the art of which the present inventor is aware. Reference to, and discussion of, these patents is intended to aid in discharging Applicant's acknowledged duty of candor in disclosing information that may be relevant to the examination of claims to the present invention. However, it is respectfully submitted that none of the above-indicated patents disclose, teach, suggest, show, or otherwise render obvious, either singly or when considered in combination, the invention described and claimed herein.

BRIEF SUMMARY OF THE INVENTION

The present invention is a novel and improved surgical method and apparatus which provides a solution to the above-described problem. Summarily stated, the present invention is an intramedullary fracture fixation device capable of being implanted in an entirely flexible condition, and after implantation locked into a rigid form when the surgeon is satisfied with the position of the fracture reduction. The device comprises, in its most essential form, a segmented flexible column made rigid by tensioning an axially disposed flexible rod. Such columns are known in the art, but not in the context of medical procedures and, most pertinently, not for use in the reduction of bone fractures. The advantage of using a flexible column for reducing a fracture is that the attending surgeon retains considerable control over the final positioning of the apparatus. If, for any reason he finds the implanted position unsatisfactory after initially locking in the configuration, the device can be unlocked, repositioned, and locked again. This procedure can be repeated until the surgeon is satisfied with the result.

The inventive apparatus is modular in form, consisting of a series of cannulated spheres and sleeves. It may be assembled either before placement in the patient's bone, or, alternatively, it may be assembled in situ.

It is therefore a first and principal object of the present invention to provide a new and improved multi-articular fracture fixation device with an adjustable modulus of rigidity.

It is another object of the present invention to provide a new and improved multi-articular fracture fixation device having modular elements that may be combined in a manner that facilitates a close fit to the particular bone dimensions at an around the fracture site.

A further object or feature of the present invention is a new and improved multi-articular fracture fixation device that may be shaped in the operating suite to fit the precise shape of the medullary canal of the patient's bone.

An even further object of the present invention is to provide a novel multi-articular fracture fixation device that is easy to remove after bone reduction and healing has been effected.

Other novel features which are characteristic of the invention, as to organization and method of operation, together with further objects and advantages thereof will be better understood from the following description considered in connection with the accompanying drawings, in which preferred embodiments of the invention are illustrated by way of example. It is to be expressly understood, however, that the drawings are for illustration and description only and are not intended as a definition of the limits of the invention. The various features of novelty that characterize the invention are pointed out with particularity in the claims annexed to and forming part of this disclosure. The invention does not reside in any one of these features taken alone, but rather in the particular combination of all of its structures for the functions specified.

There has thus been broadly outlined the more important features of the invention in order that the detailed description thereof that follows may be better understood, and in order that the present contribution to the art may be better appreciated. There are, of course, additional features of the invention that will be described hereinafter and which will form additional subject matter of the claims appended hereto. Those skilled in the art will appreciate that the conception upon which this disclosure is based readily may be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE SEVERAL VIEWS OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

Referring to FIGS. 1 through 11, wherein like reference numerals refer to like components in the various views, there is illustrated therein a new and improved multi-Articulated fracture fixation device with adjustable modulus of rigidity, generally denominated 100 herein. These views show, collectively, an adaptable and easily customized mechanical device adapted for implantation in the medullary cavity of long bone for the purpose of reducing bone fractures.

The inventive apparatus comprises, in a first aspect, a plurality of ball-and-socket type elements 110, 120, preferably including substantially spherical elements 110, and generally cylindrical elements 120. However, suitable variations may include truncated conical elements (graduated sleeve elements) 130, bullet-shaped elements 140, bifurcated bullet-shaped elements 150, and toothed cylindrical elements 160 with serrated edges 162.

Figure 3:
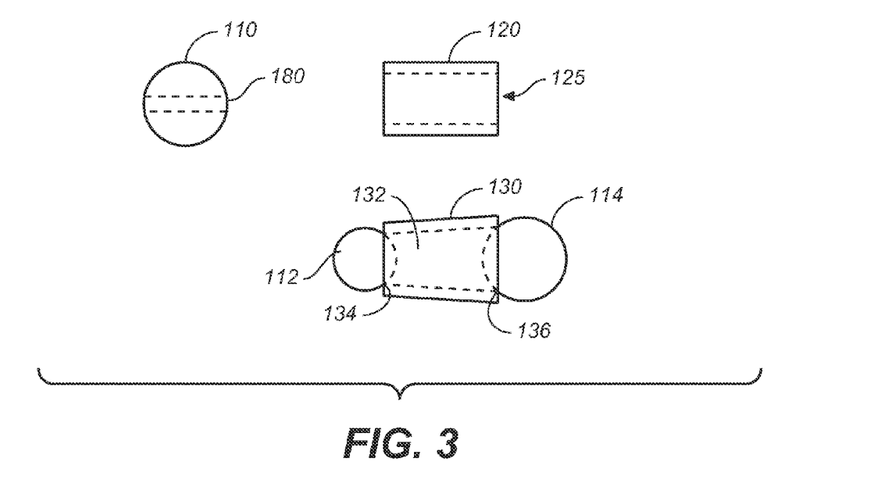
FIG. 3 is a schematic view showing the variations on the structural elements comprising the inventive apparatus.

Referring now to FIG. 3, the cylindrical elements 120 are essentially tubes of short length and include a cylindrical opening 125 extending from one end to the other. Conical elements 130 include an internal tapered through hole 132 which generally tracks (is parallel to) the tapering exterior side of the element. Accordingly, the smaller opening 134 of the conical element can be sized to accommodate a portion of a relatively small spherical element 112 (or another kind of pivotal and/or rotatable adjoining element, such as a spherical element or the spherical end of a bullet-shaped element), while the larger opening 136 can be sized to accommodate a portion of a slightly larger spherical element 114. The toothed cylindrical elements may include either a cylindrical hole 162 or a tapered hole (not shown).

Figure 4:
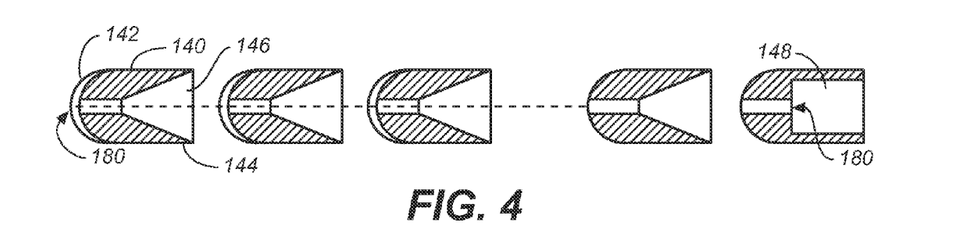
FIG. 4 is a schematic side view in elevation showing a possible alignment of ball-and-socket type elements that may be employed in the present invention.
Figure 5:
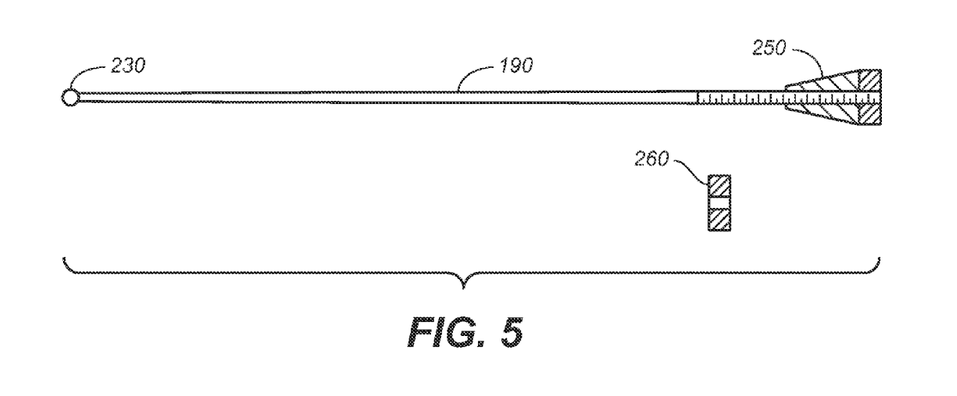
FIG. 5 is a schematic side view showing the general elements comprising a tensioning rod and locking nut as employed in the present invention.
Figure 6:
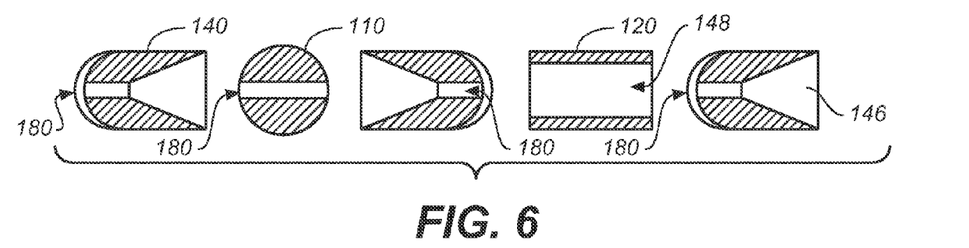
FIG. 6 is a schematic side view showing an arrangement of aligned alternative ball-and-socket elements that may be employed to form the flexible articulating column of the present invention.
Figure 7:
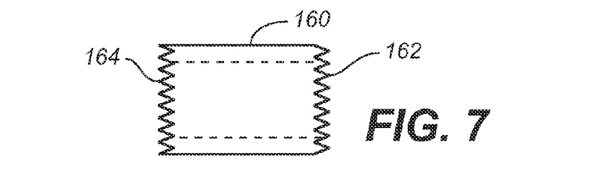
FIG. 7 is a schematic view showing an alternative segmental element including serrations on the element edges.
Figure 8:
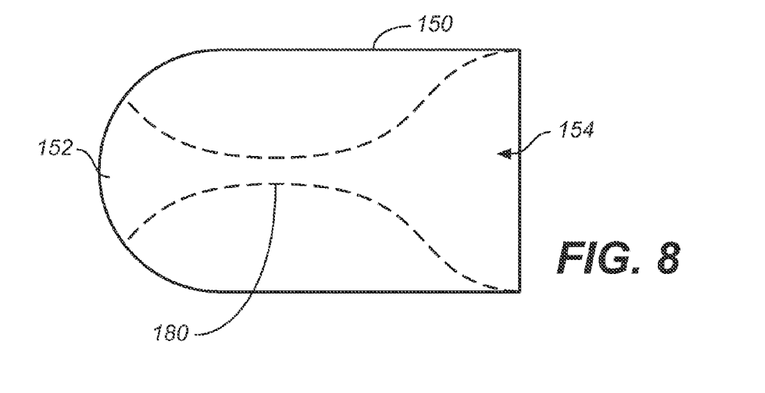
FIG. 8 is a schematic cross-section side view showing the interior hollows included in the ball-and-socket elements.
Figure 9:
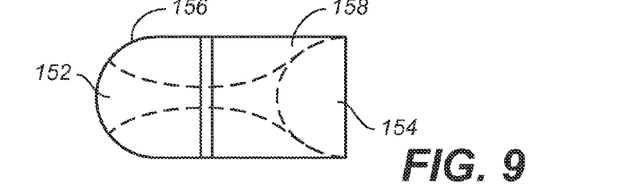
FIG. 9 is a side view showing an alternative form of the element of FIG. 8.

Referring next to FIG. 4, it will be seen that the bullet-shaped elements 140 include a spherical first end 142 and a generally planer second end 144 and are provided with a conical or domed recess or socket 146 in the second end which is adapted for cupping a swivelable adjoining element partially inserted into the socket. Alternatively, the second end of the bullet-shaped elements can be provided with a cylindrical opening 148, which accommodates a portion of a spherical element or an element having a rounded end or semi-spherical end, but retains the adjoining element relatively close to the edge of the second end.

In an alternative embodiment of the bullet-shaped element 150, both the spherical end and the planar ends include a tapered opening 152, 154, respectively. This embodiment can be bifurcated to produce two distinct new elements, including a truncated bullet-shaped element 156, and a modified cylindrical element 158. Together, these elements retain the features of the alternative embodiment of the bullet-shaped element 150, while introducing greater flexibility in designing the assembled fixation apparatus to be inserted into a medullary canal.

Figure 1:
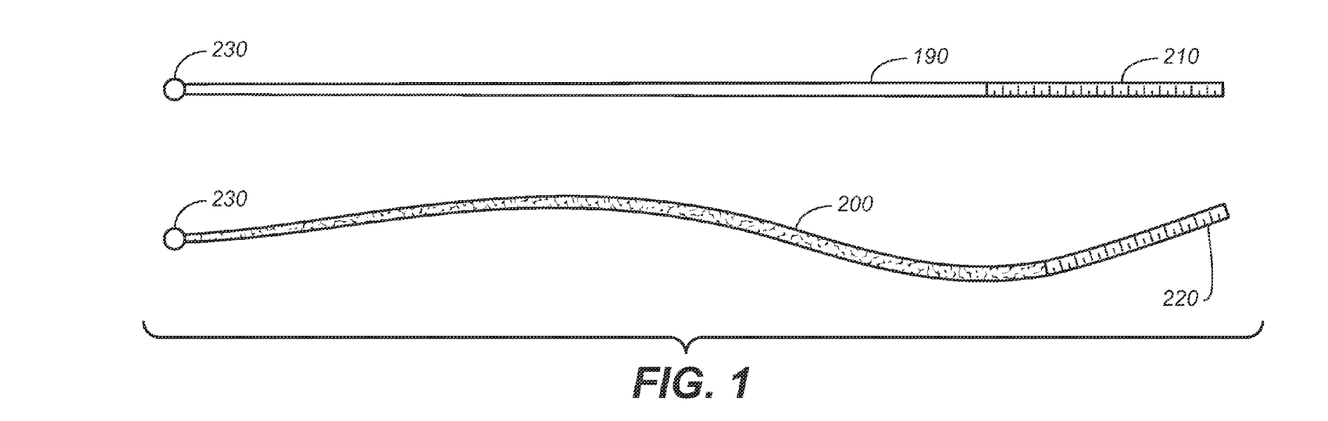
FIG. 1 is schematic side view in elevation showing the two types of tensioning members as used in the present invention, including a guide wire and a threaded cable.
Figure 2:
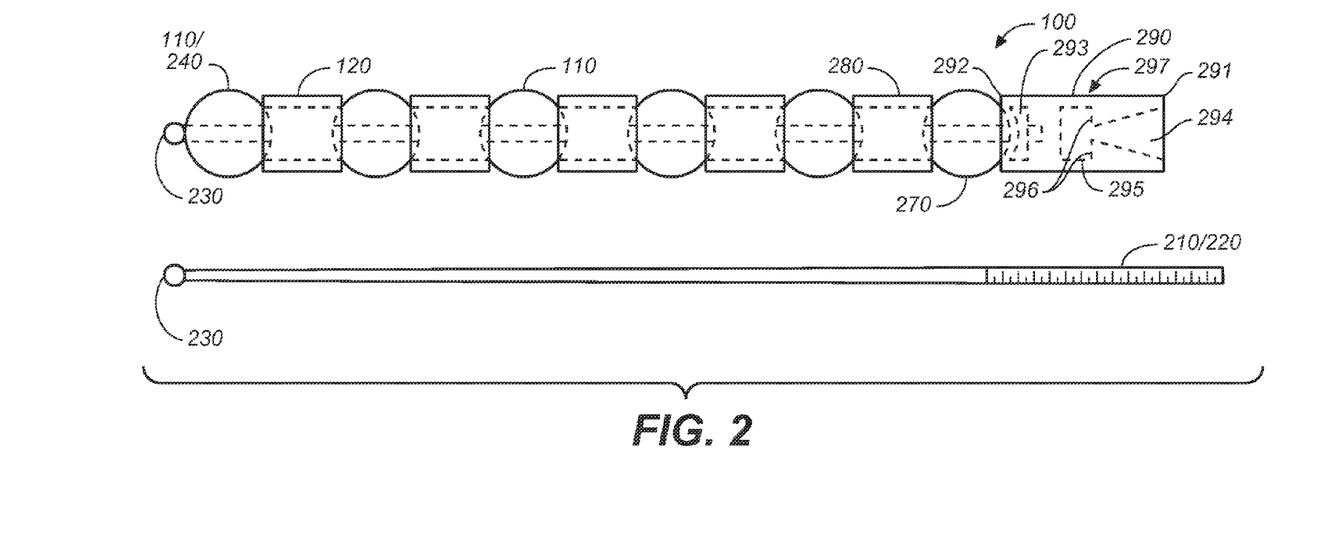
FIG. 2 is a schematic side view in elevation of a first preferred embodiment of the assembled inventive apparatus, showing the apparatus with a plurality of ball and socket elements in end-to-end alignment, an axially disposed tensioning member, as well as the openings and holes featured in each of the ball and socket elements.

All elements are provided with a through hole 180, which becomes a continuous and contiguous hole as elements are combined in a substantially end-to-end ball-and-socket assembly (see FIG. 2). A guide wire 190 or cable 200 having at least one threaded end 210/220 is inserted axially through the full length of the through hole 180 formed by the contiguous assembly elements. A stop or retention member 230, such as a ball or another kind of expansion, is disposed on the opposite end of the wire or cable, which retains the most distal element 240 and provides a fixed member against which a tensioning force may be applied.

Referring now to FIGS. 2, 5, 10, and 11, when the guide wire or threaded cable is installed through the ball-and-socket assembly, a conically-shaped compression sleeve 250 (FIG. 5) and a locking nut 260 may be placed over the threaded end to tighten down onto the proximal element 270, urging it against the adjacent element 280, and so on along the chain of elements comprising the assembly. In this manner, the column, initially flexible, becomes rigid and locked into a desired shape, whether relatively straight, slightly curved, or virtually serpentine. Thus, the ball-and-socket assembly of the apparatus has a selectively adjustable modulus of rigidity (modulus of elasticity in shear), which resists displacement to a degree governed by the compression imparted onto the tensioning elements with the lock nut tightening.

As will be seen by reference to FIGS. 2 and 12-14, the proximal terminal element in the inventive assembly comprises a compression sleeve, which in an alternative embodiment 290, includes a proximal end 291 and a distal end 292. The distal end includes a partial spherical concavity or depression 293 while the proximal end includes a tapered opening 294 which opens at its smaller end into a cylindrical void 295 having shoulders 296 substantially normal to the exterior side 297 of the sleeve.

In use, and as will be readily appreciated by those with skill in the art, the first piece placed over the wire or cable is preferably an end sphere, an expandable member, or other specialized component that will not slide beyond the end of the wire or cable, but is held captive by a ball-end retention member integrally disposed on the distal end of the wire or cable. The remainder of the implant able apparatus is assembled, alternating a sleeve with a sphere until the full desired length of the implant is attained. The compression sleeve is placed at the proximal end of the implant, and a lock nut threaded down and into the compression sleeve. A cannulated screwdriver/wrench is used to tighten the locking nut which effectively changes the device from flexible to rigid maintaining the desired shape. Excess length of the threaded wire or cable can be cut off to make the implant flush with, or embedded in, the bone.

Figure 10:
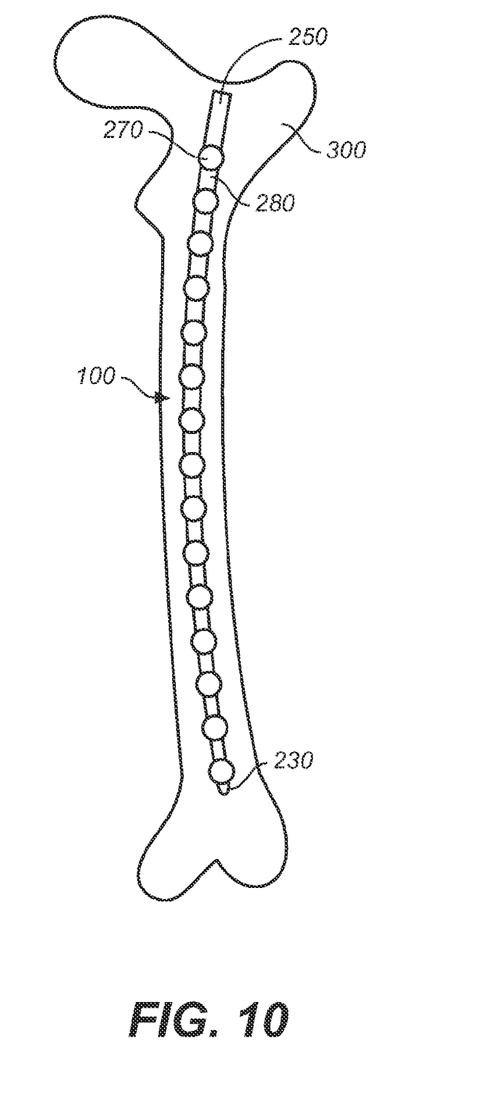
FIG. 10 is a schematic cross-sectional sagittal view in elevation showing the inventive apparatus installed in the medullary cavity of a femur.
Figure 11:
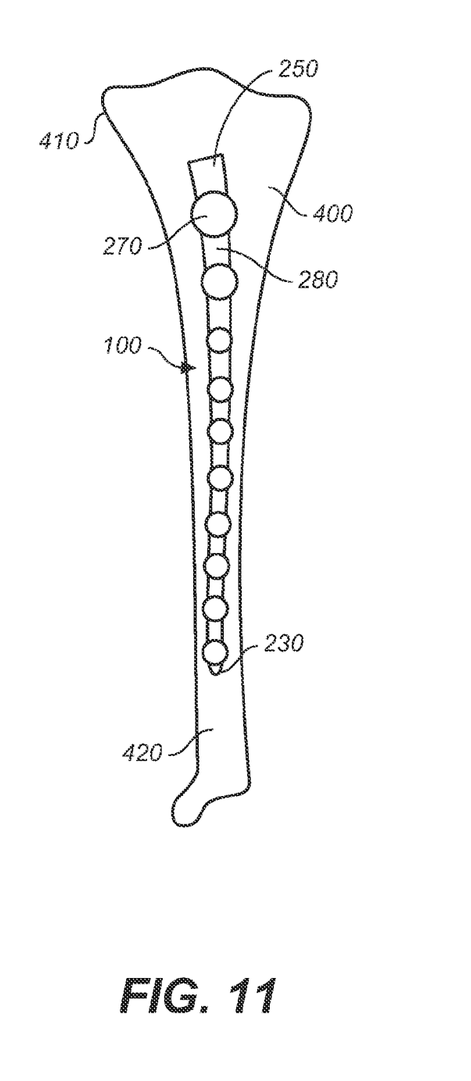
FIG. 11 is a schematic cross-sectional sagittal view showing the inventive apparatus installed in the medullary cavity of a tibia.

Referring now to FIGS. 10 and 11, it will be seen that the inventive apparatus 100 can be sized during installation to fit the medullary cavity of large elongate bones, such a femur 300, or smaller diameter bones, such as a tibia 400. In the former case, the elements may be placed in a sequence alternating spherical and cylindrical elements, and most can be of uniform size. In the latter case, it may be desirable to utilize elements of varying sizes, such that the spherical elements in the proximal portion 410 of the bone are of a larger diameter than those in the distal portion 420.

Accordingly, in its first and most essential aspect, the multi-articular fracture fixation device of the present invention includes a plurality of modular tensioning elements, including, at least, a most proximate tensioning element and a most distal tensioning element, and each of the tensioning elements has a through hole such that the elements may be disposed in a generally linear array with the through holes of the elements substantially aligned to define a continuous and contiguous through hole. In such an array, at least two of said tensioning elements are in a swiveling relationship to one another, so that those elements may be swiveled (rotated or pivoted) to create a displacement or deviation from a straight, axial alignment of the through holes. Next, the apparatus includes a flexible connecting wire having a threaded first end and a stop member affixed on a second end. In the assembled apparatus, the connecting wire is inserted through the through holes of the tensioning elements such that the tensioning elements are positioned on the connecting wire between the stop member and the threaded end. During assembly or installation, at least two of the tensioning elements may be selectively manipulated to place the through holes out of axial alignment, and when fully assembled, this will introduce a bend into the connecting wire, and thus into the array of tensioning elements. To finish the assembly, at least a lock nut is threadably disposed over the threaded first end of the connecting wire so as to engage the most proximal tensioning element and to bring the most distal tensioning element into engagement with the stop member. The lock nut is then tightened to a desired degree to set the shape and the desired modulus of rigidity of the array. Preferably, the most proximal tensioning element is a compression sleeve, as described above.

Technique of implantation: The patient is prepped for surgery, and the fracture site is approached in the standard method for intramedullary fixation. If necessary, reaming is accomplished over a guide wire. This guide wire can be the threaded connecting wire over which the rest of the implant is to be assembled, or can be exchanged for the threaded wire or cable that is part of the final assembled implant. If the implant is to be assembled within the patient the assembly is accomplished by first selecting the correct component which is to be most distal on the implant and sliding it over the cable or wire, and then alternating sleeves, spheres, and bullet-shaped or other components of the correct size until the implant is nearly to full length. A compression sleeve device is selected to complete the implant, with a nut threaded over the guide wire or cable and into the receiving end of the compression sleeve. A cannulated screwdriver or wrench is threaded over the guide wire/cable and is utilized to tighten the lock nut, effectively stabilizing the implant in rigid form. Excess guide wire/cable can be cut off to make the implant flush with the bone.

If necessary, removal of the implant is accomplished by first unlocking the device by loosening the lock nut. The implant is then extracted by any number of means, one of which might be to attach a slide hammer to internal threads within the compression sleeve and utilize the slide hammer to extract the implant. These removal techniques are facilitated by use of the tool shown in FIGS. 12-14.

Figure 12:
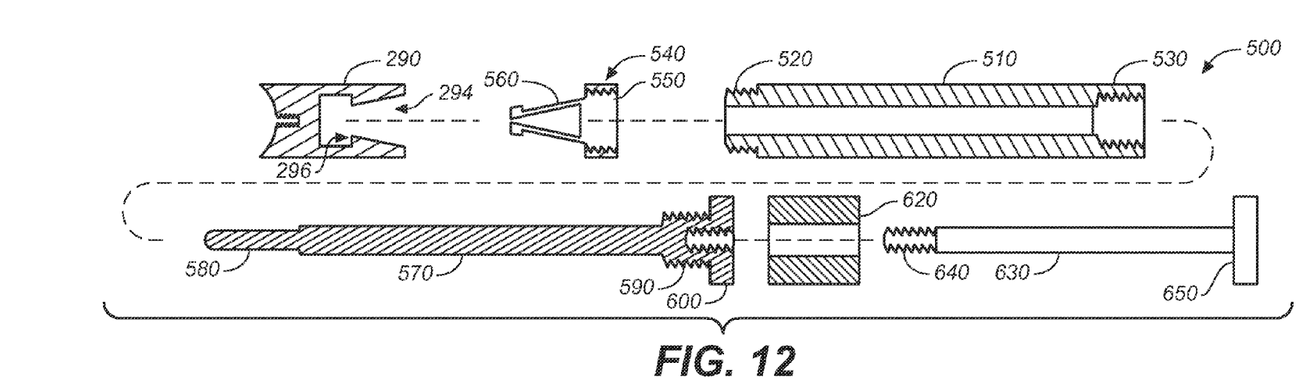
FIG. 12 is an exploded cross-sectional side view in elevation of a removal tool for use with the present invention.
Figure 13:
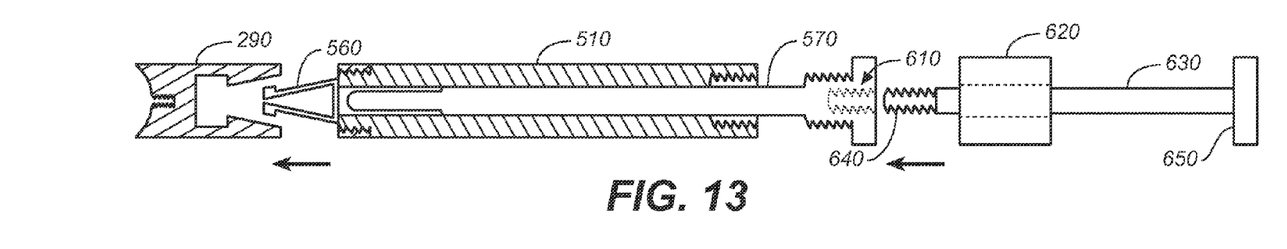
FIG. 13 is a partial cross-sectional side view showing the tool of FIG. 12 generally assembled and poised for insertion into a compression sleeve of the inventive apparatus.
Figure 14:
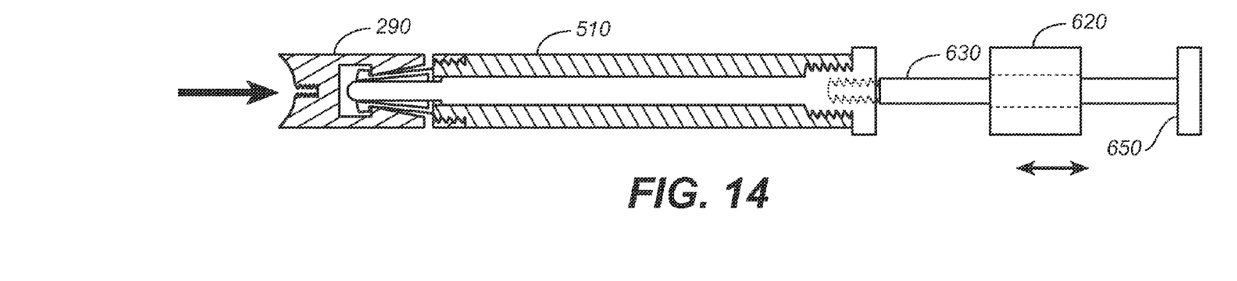
FIG. 14 is a partial cross sectional side view in elevation showing the tool of FIGS. 12 and 13 with an expansible tip inserted into a compression sleeve and configured as it would be for removal of the fracture fixation apparatus from the medullary canal of a long bone.

A preferred embodiment of a removal tool 500 for the inventive fracture reduction and fixation apparatus is adapted for use with an assembly terminated by compression sleeve 290. The tool includes a cylindrical shaft 510 having a threaded exterior surface 520 at its first end and threaded hole 530 disposed in its second end. A tip 540 includes a threaded hole 550 for threadable attachment to the shaft first end, and further includes an expansible tapered end 560 adapted to engage the shoulders 296 of compression sleeve 290 when expanded. The tool further includes a rod 570 having a rounded or tapered end 580, a threaded neck 590 immediately under a knob 600, and adapted for threadable insertion into threaded end 530 of shaft 510. The knob includes a threaded hole 610.

Next, the removal tool includes a cylindrical hammer slide 620 through which a plunger 630 is disposed, the plunger having a threaded end 640 and a gripping/percussion stop 650. The threaded end 640 is threaded into hole 610 of knob 600.

In use, after rod 570 is inserted into shaft 510, the tapered opening of the compression sleeve is located and expansible end 560 is inserted. Next, threaded neck 590 of rod 570 is screwed into the threaded opening 550 of tip 540. This expands expansible end 560 of tip 540 such that the end engages shoulders 296 of compression sleeve 290. Next, plunger 630 is inserted through hammer slide 620 and the threaded end 640 is screwed into hole 610 in knob 610. The hammer slide may then be accelerated and slammed against percussion stop 650 to tap out the multi-articular fracture fixation device.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

For instance, as will be readily apparent to those with skill in the art, a number of variations on the essential structural elements and features are possible. To begin with, the inventive apparatus may be manufactured in a variety of sizes adapted for different bone sizes, from a large femur to the fine metacarpals and metatarsals. And as indicated above, different size components of the present invention may be used within the same bone, to transition from the narrow canal at the diaphysis to the much larger canal in the metaphyseal ends of the long bone.

Different lengths of sleeve can be made available for different applications, e.g., to bridge a bony defect, or to cross an undisturbed mid-shaft.

Transitions from smaller to larger tensioning elements can be accomplished by using sleeves that are conical in shape or have another size-reducing conformation.

Different materials for all of the elements can be utilized to take advantage of their unique properties. Such material include, without limitation: Titanium, stainless steel, composites (including plastics and carbon fiber materials), Nitinol memory metal, ceramics, various bio-soluble materials, and others.

Different surface treatments may be applied to the materials to enhance their locking capabilities against adjacent structural elements. There may be some applications or instances in which bony ingrowth around the implant is desirable. In such instances, the implant may be coated before installation and/or surrounded after installation with any of, or a combination of cancellous bone allograft chips, calcium sulfate, calcium carbonate, calcium phosphate, hydroxyapatite, and demineralized bone matrix. Alternatively, the adjustable elements may be made with a porous titanium surface, such as has been used to fixate prostheses in joint replacement surgery.

In the more likely situation, when it is desirable to prevent bony ingrowth so that removal of the implant is facilitated, the device is made of material that is biologically inert and exquisitely smooth on its surface, such as a ceramic coating, at least in areas of the outer surface of the implant that will contact bone. The areas where the implant component pieces articulate with one with another may be provided with a different surface treatment to enhance the desired rigidity of the final construct.

To enhance bone healing, it is possible to apply a small electrical charge across the fracture through utilization of proper materials and a miniature battery and electrodes.

To effect a small electrical charge across the fracture site, use of dissimilar metals and a design to accommodate the desired effect in the device may be employed.

Next, the flexibility or rigidity of the inventive apparatus can be adjusted by the tightness of the lock nut at its proximal end. A torque-sensitive wrench can be supplied to assist in determining the relative modulus of rigidity of the implant.

A remote-control device can be employed to enable unlocking and re-locking the device within the patient, should adjustment be necessary post-operatively, thus allowing for non-surgical or non-invasive realignment.

A bio-soluble washer can be applied beneath the locking nut, such that the implant slowly loses rigidity, thereby allowing more biomechanical forces to be transferred to the bone over time, while the implant shares less of the load.

The entire device can be manufactured of bio-soluble materials, obviating the need for subsequent removal.

A spring-loaded nut assembly can be applied to ensure that the device maintains its rigidity throughout its implanted life.

An expandable component can be placed at the distal end of the implant, to lock the implant in place distally.

An expandable component can be placed at the proximal end of the implant, to lock the implant in place proximally.

An expandable component may be placed at both ends of the implant, thereby converting the implant into a compressive device along its length, by forcing the bone to shorten as the implant is locked.

A component with various holes can be placed either distally or proximally or both, and can accommodate wires or screws to enhance fixation, or allow for a buttress effect.

In view of the foregoing variations, the above description and illustrations should not be construed as limiting the scope of the invention, which is defined by the appended claims.

What is claimed as invention is:

1. A multi-articular intramedullary fracture fixation device, comprising:

a plurality of modular tensioning elements, including, at least, a compression sleeve in the position of a most proximate tensioning element and a most distal tensioning element, each of said tensioning elements having a through hole, and disposed in a generally linear ball-and-socket array such that the through holes are substantially aligned to define a continuous and contiguous through hole, wherein at least two of said tensioning elements are in a swiveling relationship to one another, and wherein said compression sleeve includes an exterior side, a distal end having a partial spherical concavity, and a proximal end having a tapered hole which opens at its small end into a cylindrical void having shoulders substantially normal to said exterior side of said compression sleeve;

a flexible connecting wire having a threaded first end and a stop member affixed on a second end, said connecting wire inserted through the through holes of said tensioning elements such that said tensioning elements are disposed between said stop member and said threaded first end, and wherein at least two of said tensioning elements may be selectively manipulated by a user to place the through holes of said tensioning elements out of axial alignment and to bend said connecting wire; and a lock nut threadably disposed over said threaded first end of said connecting wire so as to engage said most proximal tensioning element and to bring said most distal tensioning element into engagement with said stop member, and wherein said lock nut may be selectively tightened or loosened to adjust the modulus of rigidity of said array.

* * * * *